United States Patent [19]

Christensen et al.

[11] 4,035,359

[45] July 12, 1977

[54] 6α, β-SUBSTITUTED PENICILLIN DERIVATIVES

[75] Inventors: Burton G. Christensen, Scotch Plains; Lovji D. Cama, Edison, both of N.J.

[73] Assignee: Merck & Co., Inc., Rahway, N.J.

[21] Appl. No.: 599,266

[22] Filed: July 25, 1975

Related U.S. Application Data

[60] Division of Ser. No. 495,010, Aug. 5, 1974, which is a continuation-in-part of Ser. No. 149,349, June 2, 1971, abandoned.

[51] Int. Cl.² .................................... C07D 499/46
[52] U.S. Cl. ......................... 260/239.1; 424/271
[58] Field of Search ...................... 260/243 C, 239.1

[56] References Cited

U.S. PATENT DOCUMENTS 3,897,424  7/1975  Koppel et al. ............... 260/243 C Primary Examiner—Nicholas S. Rizzo
Assistant Examiner—David E. Wheeler
Attorney, Agent, or Firm—Hesna J. Pfeiffer; Edmunde D. Riedl

[57] ABSTRACT

Novel 6-methoxy and 6-thioalkyl-6-acylamido-penicillanic acids and their non-toxic pharmaceutically-acceptable salts, esters and amides which are useful as antibiotics. The products are prepared by treating an ester of 6-substituted-6-aminopenicillanic acid with an acylating agent followed by removal of the ester group. Also disclosed are novel intermediates.

6 Claims, No Drawings

6α, β-SUBSTITUTED PENICILLIN DERIVATIVES

CROSS-REFERENCE TO RELATED APPLICATIONS

This is a division of application Ser. No. 495,010, filed Aug. 5, 1974 which in turn is a continuation-in-part of copending application Ser. No. 149,349, filed June 2, 1971, now abandoned.

BACKGROUND OF THE INVENTION

This invention relates to new antibiotics, new intermediate products useful in the preparation of these antibiotics, and processes for the preparation of these compounds. More particularly, it is concerned with new 6-aminopenicillanic acid derivatives having a methoxy or thioalkyl substituent at position 6, and new intermediates and processes for their production.

The discovery of penicillin, which was found to be such an important and effective antibiotic, stimulated great interest in this field. Subsequently, various other antibiotics such as streptomycin, the tetracyclines, novobiocin, and the like were found which greatly increased the doctor's armamentarium for treating infections due to a variety of pathogens. Unfortunately, the use of these antibiotics gave rise to strains of pathogens resistant to these known antibiotics. In addition, the known antibiotics suffer from the disadvantages that they are only effective against certain types of microorganisms and are not effective against a broad range of pathogens. Accordingly, the search for other antibiotics has continued.

It is an object of this invention to provide new penicillins having antibiotic activity. A further object is to provide processes for the preparation of these new antibiotics. Another object is to provide new intermediates useful in preparing these new penicillins. Other objects will be apparent from the detailed description of this invention hereinafter provided.

The new penicillins of the present invention are compounds wherein the penam nucleus, namely a thioazolidine ring with a fused β-lactam, contains a methoxy or thiomethyl substituent at the 6-position. Thus, these new penicillins which can be represented by the structural formula:

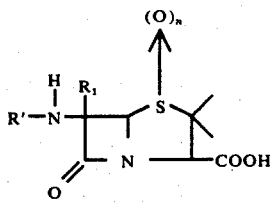

wherein R' represents an acyl group and $R_1$ is methoxy or thioloweralkyl of 1–6 carbon atoms; $n$ is 0 or 1; and derivatives thereof, such as esters, amides, and salts, are valuable new antibiotic substances. Compounds wherein $R_1$ is thiolower alkyl are also valuable as intermediates to make the 6-methoxy compounds. Compounds where $n=1$ are also valuable intermediates to make novel cephalosporins.

The acyl radical represented by R' can be a substituted or unsubstituted aliphatic acyl, aromatic acyl, heterocyclic acyl, araliphatic acyl or heterocyclylaliphatic acyl radical derived from a carboxylic acid or a carbothioic acid such as the acyl radicals of the known cephalosporins and penicillins. These acyl radicals can be represented by the general formula:

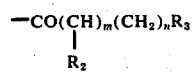

where $R_2$ is a radical of the group defined below, $m$ and $n$ represent 0–4 and $R_3$ represents R" or ZR", which are defined below.

One group of acyl radicals can be represented by the acyl group general formula:

wherein R" represents a substituted or unsubstituted straight or branched chain alkyl, alkenyl or alkynyl; aryl; aralkyl; cycloalkyl; heteroaryl or heteroaralkyl. These group can be unsubstituted or can be substituted by radicals such as alkyl, alkoxy, halo, cyano, carboxy, sulfoamino, carbamoyl, sulfonyl, azido, amino, substituted amino, haloalkyl, carboxyalkyl, carbamoylalkyl, N-sutstituted carbamoylalkyl, guanidino, N-substituted guanidino, guanidinoalkyl, and the like. Representative examples of such acyl groups that might be mentioned are those wherein R" is benzyl, p-hydroxybenzyl, 4-amino-4 -carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-metyl-4 -isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, D-4-amino-4-carboxybutyl, D-4-N-benzoylamino-4-carboxy-n-butyl, p-aminobenzyl, o-aminobenzyl, m-aminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4 -methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(5-carbamoylthienyl)-methyl, 2- or 3-(5-methylthienyl)methyl, 2- or 3-(5-methoxythienyl)methyl, 2- or 3-(5-chlorothienyl)methyl, 2- or 3-(5-sulfothienyl)methyl, 2- or 3-(5-carboxythienyl)-methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, and 1-tetrazolylmethyl.

The acyl group can also be a radical of the formula:

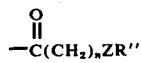

wherein n is an integer of 0–4, Z is oxygen or sulfur, and R'' is defined as above. Representative members of the substituent

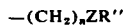

that might be mentioned are allylthiomethyl, phenylthiomethyl, butylmercaptomethyl, α-chlorocrotylmercaptomethyl, phenoxymethyl, α-phenoxyethyl, αphenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-carboxymethyl)-phenylthiomethyl, 2-thiazolylthiomethyl, p-(sulfo)phenoxymethyl, p-(sulfo)phenylthiomethyl, p-(carboxy)phenoxymethyl, -(carboxy)phenylthiomethyl, p-(carboxymethyl)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, 6,8-bis(methylthio)octoanoyl.

Alternatively, the acyl group can be a radical of the formula:

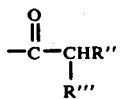

wherein R'' is defined as above and R''' is amino, hydroxy, azido, carbamoyl, guanidino, acyloxy, halo, sulfamino, tetrazolyl, sulfo, carboxy or carbalkoxy. Representative members of the substituent

that might be mentioned are α-aminobenzyl, α-amino-2-thienylmethyl, α-methylaminobenzyl, α-amino-γ-methylmercaptopropyl, α-amino-3 or 4-chlorobenzyl, α-amino-3 or 4-hydroxybenzyl, α-amino-2,4-dichlorobenzyl, α-amino-3,4-dichlorobenzyl, D(—)-α-hydroxybenzyl, α-carboxybenzyl, α-amino-3thienylmethyl, D(—)-α-amino-3-chloro-4-hydroxybenzyl, D(—)-α-amino-3-thienylmethyl, 1-aminocyclohexyl, α-(5-tetrazolyl)-benzyl, α-sulfaminobenzyl, α-sulfamino-3-thienylmethyl, α-(N-methylsulfamino)benzyl, D(—)-α-guanidino-2-thienylmethyl, D(—)-α-guanidinobenzyl, αguanylureidobenzyl, α-hydroxybenzyl, α-azidobenzyl, α-fluorobenzyl, 4-(5-methoxy-1,3oxadiazole)-aminomethyl, 4-(5-methoxy-1,3-oxadiazole)-hydroxymethyl, 4-(5-methoxy-1,3-oxadiazole)-carboxymethyl, 4-(5-methoxy-1,3-sulfadiazole)-aminomethyl, 4-(5-methoxy-1,3sulfadiazole)-hydroxymethyl, 4-(5-methoxy-1,3-sulfadiazole)-carboxymethyl, 2-(5-chlorothienyl)-aminomethyl, 2-(5-chlorothienyl)-hydroxymethyl, 2-(5-chlorothienyl)-carboxymethyl, 3-(1,2-thiazole)-aminomethyl, 3-(1,2-thiazole)-hydroxymethyl, 3-(1,2-thiazole)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, 2-azidooctyl-3-phenyl-3-azidomethyl, α-phosphonobenzyl and α-sulfobenzyl.

Alternatively, the group

can be a sulfonamido group such as phenylsulfonamido, ethylsulfonamido, benzylsulfonamido, 2,5-dimethylsulfoamido, 4-chlorosulfonamido, 4-chlorophenylsulfonamido, 4-methoxysulfonamido, and the like.

The acyl substituents of the general formula:

wherein $R_{10}$ and $R_{11}$ are as defined below represent a preferred group of substituents because of their generally enhanced antibiotic activity. $R_{10}$ is hydrogen, amino, guanidino, hydroxy, carboxy, tetrazolyl, sulfo or sulfamino. $R_{11}$ is phenyl, substituted phenyl, a monocyclic 5- or 6-membered heterocyclic ring containing one to four hetero atoms selected from oxygen, sulfur, nitrogen or phenylthio.

Examples of these preferred acyl substituents that might be mentioned are phenylacetyl, 4-carboxylmethylphenylacetyl, 2-carboxyphenylacetyl, 2-methyl-2-phenoxyacetyl, 3-furylacetyl, 2-thienylacetyl, phenoxyacetyl, 3-thienylacetyl, 3-isothiazolylacetyl, 4-isothiazolylacetyl, phenylthioacetyl, 4-pyridylthioacetyl, tetrazolylacetyl, α-fluorophenylacetyl, D-phenylglycyl, 3-hydroxy-D-phenylglycyl, 2-thienylglycyl, 3-thienylglycyl, phenylmalonyl, 3-thienylmalonyl, α-sulfaminophenylacetyl, α-hydroxyphenylacetyl, α-tetrazolylphenylacetyl and α-sulfophenylacetyl.

The new penicillins of this invention can be used as antibiotics in the form of derivatives such as metal salts, for example, sodium potassium or ammonium salts, amine salts, for example, procaine, or N,N'-dibenzylethylenediamine salts, or amides and substituted amides, as is well known in this art.

Alternatively, labile esters which are metabolized readily such as groups of the formula —CH$_2$OCO(CH$_2$-)$_n$—A where n is an integer from 0 to 5 and A is an unsubstituted or substituted aliphatic, alicyclic, aromatic or heterocyclic radical represent preferred species of ester derivatives suitable for use in antibiotic therapy. Other esters of the new penicillins such as lower alkyl, aralkyl, aryl, silyl, halo lower alkyl, or stannyl esters are suitable for use as intermediates in preparing the free acid and salts thereof in accordance with methods known in this art.

In accordance with the present invention, it is now found that the new penicillins of this invention can be prepared by processes which can be depicted as follows:

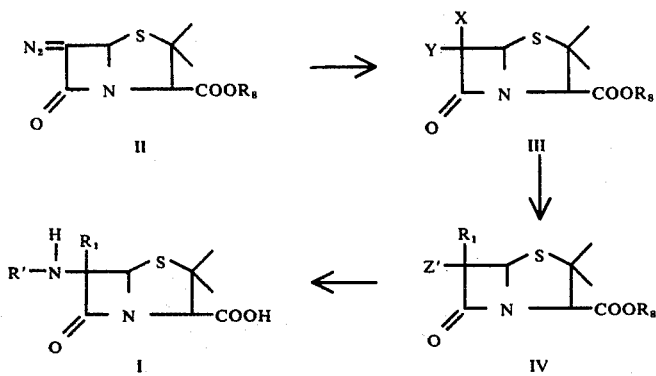

In the foregoing flowsheet the starting compound is a derivative of 6-diazopenicillanic acid wherein the carboxy group is preferably blocked, for example, by forming a suitable ester. These 6-diazopenicillanic acid esters are readily prepared by esterifying 6-aminopenicillanic acid and reacting the ester with nitrite. Thus, the 6-aminopenicillanic acid can be esterified in accordance with methods well known in this art to obtain, for example, the esters wherein $R_8$ represents an alkyl group such as methyl, t-butyl, and the like, a haloalkyl group such as trichloroethyl, an alkenyl group such as allyl, an alkynyl group such as propargyl, an aralkyl group such as benzyl, p-methoxybenzyl, o-nitrobenzyl, an organometallic group, for example, a silyl group such as trimethylsilyl, or a stannyl group such as tributyltin or phenacyl. The 6-diazopenicillanic acid ester (II) is converted by reaction with a compound of the formula: XY, to form intermediate product (III) wherein X represents halogen and Y is a nitrogenous substituent or $R_1$. Similarly a mixture of compounds one of which is the source of a positive halogen is an N-haloamide such as N-bromosuccinimide, N-bromophthalimide or N-bromoacetamide or halo and the other of which is a source of Y. Intermediate compound (III) is then converted to compound (IV) in which Z' represents a nitrogenous group which is readily convertible to amino or acylamino. Compound (IV) is then converted to the desired penicillin ester which can be reacted to obtain the corresponding penicillin acid or a salt thereof. The processes for carrying out the various steps of the foregoing flowsheet will be more readily understood from the detailed descriptions of methods which can be used to carry out these processes.

Thus, in accordance with one specific embodiment of this invention, the new penicillins are obtained by the following processes:

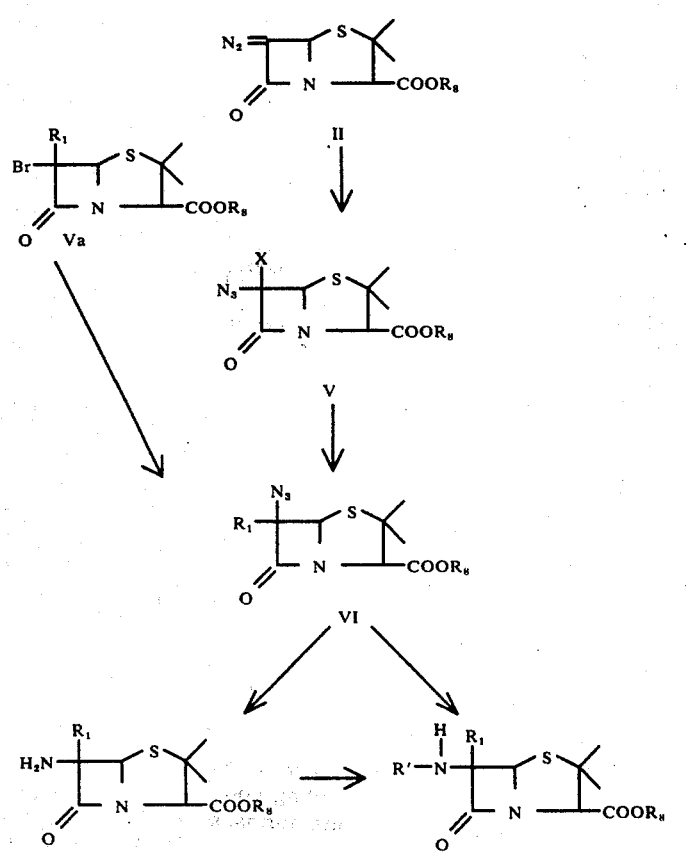

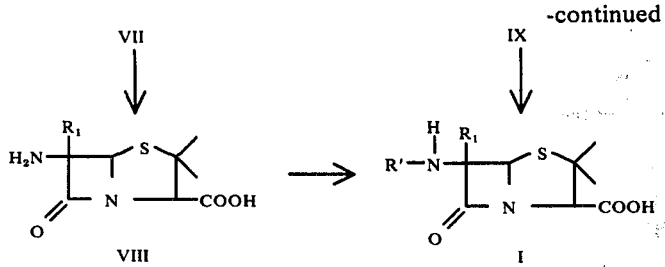

In the one variation of the above process the diazopenicillanic acid ester (II) is reacted with a halo azide from the group consisting of bromine, chlorine, or iodine azide, preferably in the presence of a tertiary amine azide, to produce the intermediate 6-halo-6-azidopenicillanic acid ester (V) which on reaction with a suitable nucleophilic reagent such as methanol or loweralkyl sulfenyl bromide, is converted to the desired 6-$R_1$-6-azidopenicillanic acid ester (VI). Alternatively, II is treated with an alcohol or thiol hyophalite to give Va which is treated with azide anion to give VI. This intermediate product is reduced and acylated in one step to form the substituted penicillanate ester (IX) which can then be cleaved to remove the blocking group and obtain the penicillanic acid or a salt thereof (X). Alternatively, as shown in the flowsheet, the 6-$R_1$-6-azidopenicillanic acid ester (VI) is reduced to the 6-$R_1$-6-aminopenicillanic acid ester (VII) which can be acylated to produce the 6-$R_1$-6-acylaminopenicillanic acid ester (IX), or the ester group of compound (VII) can be cleaved to obtain the free acid (VIII) which can by acylated to form the desired substituted penicillanic acid or a salt thereof. The step of cleaving the blocking group is readily effected in accordance with methods known in this art. For example, an aralkyl group such as the benzyl ester is removed by reduction, a silyl ester can be removed by hydrolysis to form the free acid or a salt thereof. In this process other esters which are readily cleaved to form the free acid as trichloroethyl, p-methoxybenzyl, o-nitrobenzyl, phenacyl and t-butyl and the like can be used.

The step of producing the halo azide intermediate is carried out by reacting the diazo compound with a halo azide at a temperature between about 0° and −50° C. for sufficient time to complete the formation of the desired compound. The reaction is preferably carried out in a suitable organic solvent medium which is inert to the reactants. Various solvents which do not contain an active hydrogen such as methylene chloride, chloroform, benzene, toluene, ether and the like, or mixtures thereof provide suitable mediums for carrying out the reaction. Generally, it is preferred to effect the reaction in the presence of a second azide such as lithium azide or a tertiary ammonium azide, for example triethylammonium azide, since under these conditions the formation of the undesired 6-dibromo compound is avoided. The halo azide is used in an amount in slight excess of stoichemetric requirements. The amount of second azide is not critical and it is generally desirable to use an excess in order to obtain maximum yields of the desired halo azido compound under optimum conditions. After completion of the formation of the halo azide the produce is recovered and can be purified further, for example by chromatography, in accordance with processes well known in this art.

The next step of the process, comprising the replacement of the halo substituent, is effected by reacting the halo azide with a substance capable of furnishing the methoxy or thiomethyl group to replace the halo. This reaction can be carried out in the presence of a suitable nonreactant solvent such as methylene chloride, chloroform, benzene, toluene, ether, petroleum, ether and the like, or preferably using the nucleophile itself, e.g., methanol, as solvent. The reaction is preferably carried out in the presence of a suitable acid scavenger such as an alkali or preferably a tertiary amine such as pyridine or a silver salt such $Ag_2O$, $AgBF_4$, $AgOSO_2CF_3$.

In the next step of the above-described process the 6-azido-6-$R_1$ compound is then reduced to afford the corresponding 6-amino-6-$R_1$ compound. Various methods of carrying out this reduction can be employed, but it is generally preferred to carry out the reduction of the azido to the amino group by catalytic hydrogenation employing a nobel metal catalyst such as platinum, palladium or oxides thereof. These processes are carried out in accordance with procedures well known in this art. Alternatively, the reduction can be effected in the presence of a suitable acylating agent to produce the desired 6-acylamido-6-$R_1$ compound. The 6-amino compound can be reacted with suitable acylating agents using procedures well known in this art to obtain the desired 6-acylamido compounds.

The sulfoxide form of the penicillin (n=1) is prepared by oxidizing a penicillin using oxidizing agents known in the art, or by oxidizing the 6-amino-6-$R_1$-penicillin intermediates and then acylating.

EXAMPLE 1

6β-Acetamido-6-methoxypenicillanic Acid and Sodium Salt

Step A: Benzyl 6-Diazopenicillanate

Benzyl 6-aminopenicillanate p-toluene sulfonic acid salt (0.5 g.) is added to a mixture of methylene chloride (50 ml.), ice (50 cc.) and sodium nitrite (1.5 g.) and the mixture is thoroughly mixed. To the resulting mixture is added a total of 0.2 g. of p-toluenesulfonic acid in three equal amounts at intervals of 5 minutes, and the cold mixture (10° C.) is again mixed by shaking for 20 minutes. The yellow methylene chloride solution of benzyl 6-diazopenicillanate is then separated, dried over sodium sulfate at 0°–10° C., filtered and the dried solution is evaporated at room temperature to about 5 ml.

Step B: Benzyl 6β-azido-6-bromopenicillanate

To a solution of benzyl 6-diazopenicillanate (2.0 g.) in methylene chloride (20 ml.) is added nitromethane (20 ml.) followed by triethylammonium azide solution (20 ml.) The resulting reaction mixture is cooled to 5° C., and to this cooled solution is added 20 ml. of bromine azide solution over a period of 15 seconds. To the resulting cooled reaction mixture is added 50 ml. of tenth normal sodium thiosulfate solution with vigorous agitation. After stirring for 2 additional minutes, the solution gives a negative test with starch iodide paper. Sodium bicarbonate is then added to the solution, and the mixture is stirred until $CO_2$ evolution ceases. The organic phase is separated, and the aqueous phase is extracted with 20 ml. of methylene chloride. The combined organic phase is washed with saturated sodium bicarbonate solution until no more evolution of $CO_2$ occurs. The organic phase is then dried over magnesium sulfate and evaporated to dryness to give 1.3 g. of crude benzyl 6-azido-6-bromopenicillanate.

The crude product is purified by absorbing it on 2.5 g. of silica gel, placing the absorbate on top of a column of 50 g. of silica gel in a mixture of equal parts of hexane and benzene, developing the column with the same solvent, collecting 200 ml. fractions of eluate, and recovering a solution of benzyl 6β-azido-6-bromopenicillanate (0.550 g.) from fractions 5–10. This product has a $R_f$ of 0.60 ($CHCl_3$).

IR: 4.69μ (azido), 5.53μ (β-lactam structure) and at 5.71μ (ester)

NMR: 2.62 tau (s), (phenyl); 4.7 tau (s), (5H); 4.79 tau (s), ($CH_2.C_6H_5$); 5.47 tau (s), (3H); 8.41 tau (s); 8.63 tau (s), (gem $CH_3$). [(s) denotes singlet]

The triethylammonium azide solution is prepared by dissolving sodium azide (3.0 g.) in water (10 ml.) cooling this solution to 0°–10° C., adding methylene chloride (20 ml.) and then concentrated sulfuric acid (3.0 ml.) dropwise with rapid stirring, separating the organic phase, extracting the aqueous phase with methylene chloride (5.0 ml.), drying the combined aqueous phases over calcium chloride and adding triethylamine to the dried solution until the pH is 7.0.

The bromine azide solution is prepared by cooling a mixture of sodium azide (5.3 g.) and methylene chloride (16.0 ml.) to 5° C., adding bromine (1.28 g.) to the cooled mixture followed by concentrated hydrochloric acid (4.0 ml.) and allowing the stoppered mixture to stir at 0°–10° C. for three hours. The organic phase is separated from the phase-like inorganic phase. The inorganic phase is washed with methylene chloride (4.0 ml.) and the organic phases are combined to give 20 ml. of solution.

Step C: Benzyl 6β-azido-6-methoxypenicillanate

To a solution of 0.55 g. of benzyl 6β-azido-6-bromopenicillanate in 50 ml. of methanol is added 0.334 g. of silver tetrafluoroborate, and the stoppered mixture is allowed to stir at room temperature for 2½ hours. The methanol is then removed under reduced pressure, and the residue is taken up on 30 ml. of methylene chloride, filtered through diatomaceous earth and washed with a small quantity of methylene chloride. The filtrate and washing are washed once with a 5% solution of sodium bicarbonate and then brine, dried and evaporated to give 0.464 g. of crude benzyl 6-azido-6-methoxypenicillanate. This product is purified by chromatography on 15 g. of silica gel, and the column is developed with 70% hexane/benzene. The eluate is collected in 50 ml. fractions and fractions 12–26 evaporated to obtain benzyl 6,6-dibromopenicillanate. The column is then eluted with 70% benzene in hexane and fractions 28–39 evaporated to yield 0.325 g. of desired product, benzyl 6β-azido-6-methoxypenicillanate. This product has a $R_f$ of 0.435 ($CHCl_3$); IR, 4.70μ (azido), 5.58μ (β-lactam), and 5.71μ (ester); and NMR in $CDCl_3$ 2.62 tau (s), (phenyl); 4.60 tau (s), (5H); 4.78 tau (s), ($CH_2C_6H_5$); 5.47 tau (s), (3H); 6.35 tau (s), ($OCH_3$); and 8.4 tau (s) and 8.58 tau (s), (gem $CH_3$).

Step D: Benzyl 6β-acetamido-6-methoxypenicillanate

To a solution of 0.065 g. of benzyl 6-azido-6-methoxypenicillanate in 20 ml. of acetic anhydride is added 0.065 g. of platinum oxide, and the mixture is hydrogenated at atmospheric pressure for 18 hours. The resulting solution is concentrated under reduced pressure at a temperature below 40° C. to remove the acetic anhydride. The resulting residue is taken up in a mixture of equal volumes of methylene chloride and ethyl ether and filtered through diatomaceous earth to remove the catalyst. The filtrate and washings are evaporated under reduced pressure to afford 0.066 g. of benzyl 6β-acetamido-6-methoxypenicillanate. The crude product is purified by thin layer chromatography to yield 0.03 g. of pure product. $R_f$ of 0.52 (2% $CH_3OH/CHCl_3$);

IR: 5.59μ (β-lactam) and 5.71μ (ester).

NMR: 2.63 tau (s), (phenyl); 4.4 tau (s), (5H); 4.80 tau (s) ($CH_2C_6H_5$); 5.52 tau (s), (3H); 6.53 tau (s), ($OCH_3$); 7.9 tau (s),

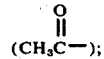

8.45 tau (s) and 8.60 tau (s), (gem $CH_3$).

Step E: 6β-Acetamido-6-methoxypenicillanic Acid and Sodium Salt

A solution of benzyl 6β-acetamido-6-methoxypenicillanate (0.03 g.) in a mixture of dioxane (2 ml.), methanol (4ml.) and water (2 ml.) is hydrogenated using 10% palladium on charcoal (0.03 g.) at 40 p.s.i. for one hour. The catalyst is removed and the solvents are removed in vacuo at room temperature. To the residue of 6β-acetamido-6-methoxypenicillanic acid is added a solution of sodium bicarbonate (0.03 g.) in water (10 ml.). The bicarbonate solution is washed with methylene chloride and the aqueous phase freeze dried to afford sodium 6β-acetamido-6-methoxypenicillanate. This compound shows a zone of inhibition against B-Subtilis.

EXAMPLE 2

Benzyl 6β-acetamido-6-methoxypenicillanate

Step A: Benzyl 6-methoxy-6-aminopenicillanate

To a solution of benzyl 6-azido-6-methoxypenicillanate (0.045 g.) in ethyl acetate (8.0 ml.) is added 0.045 g. of 10% palladium-on-charcoal. The mixture is reduced under hydrogen at atmospheric pressure for 20 hours. The catalyst is removed by filtration and the filtrate evaporated to dryness to afford crude benzyl-6-methoxy-6-aminopenicillanate. Thin layer chromatography shows one major spot, $R_f$ 0.52 (2% methanol, chloroform, silica gel plates). The spot gives a positive ninhydrin test. When this product is further purified by thin layer chromatography, the product obtained exhibits, in its infrared spectrum, a β-lactam and an ester carbonyl at 5.59 and 5.71μ, respectively, and N–H at 2.90μ. No azide function is observed.

Step B: Benzyl 6β-acetamido-6-methoxypenicillanate

Benzyl 6-methoxy-6-aminopenicillanate is treated with acetic anhydride (2.0 ml.) for one hour at room temperature. The acetic anhydride is then evaporated under reduced pressure and the residue purified by preparative thin layer chromatography to afford product having β-lactam, ester and amide carbonyl in the infrared and a $R_f$ on thin layer chromatography essentially identical to that of benzyl 6β-acetamido-6-penicillanate obtained in Example 1, Step D.

EXAMPLE 3

6β-Phenylacetamido-6-methoxypenicillanic Acid Sodium Salt

Step A: Benzyl 6β-phenylacetamido-6-methoxypenicillanate

To a solution of benzyl 6-β-azido-6-methoxypenicillanate (0.5 g.), phenylacetic anhydride (2.5 g.) and dioxane (20 ml.) is added platinum oxide (0.25 g.) and the resulting mixture is hydrogenated at atmospheric pressure for 20 hours. The dioxane is removed under reduced pressure, and the residue is chromatographed on 30 g. of silica gel. The column is developed with benzene to remove unreacted phenylacetic anhydride and any unreacted azide. The column is eluted with chloroform, and five 50 ml. fractions of eluate are evaporated to afford the crude product mixed with phenylacetic acid. The crude product is dissolved in 30 ml. of methylene chloride, washed once with 5% solution of sodium bicarbonate, dried over magnesium sulfate and evaporated to afford 0.175 g. of the benzyl ester of 6-methoxy benzylpenicillin. This product is chromatographed on silica gel using a methylene chloride-ethyl acetate gradient to obtain 0.06 g. of pure benzyl 6β-phenylacetamido-6-methoxypenicillanate. This product has a $R_f$ of 0.434 (2% $CH_3OH/CHCl_3$); IR, 5.59μ (β-lactam), 5.71μ (ester), 5.95μ (amide I) and 6.58 μ (amide II); NMR, 2.65 tau (s), ($C_6H_5$); 4.41 tau (s), (5–H); 4.81 tau (s), ($OCH_2C_6H_5$); 5.59 tau (s), (3H); 6.35 tau (s), ($COCH_2C_6H_5$); 6.60 tau (s), (O C $H_3$); and 8.64 tau (s), (gem $CH_3$).

Step B: 6β-Phenylacetamido-6-methoxypenicillanic Acid Sodium Salt

To a solution of benzyl 6β-phenylacetamido-6-methoxypenicillanate (0.317 g.) in a mixture of dioxane (9.0 ml.), methanol (5.0 ml.) and water (10 ml.) is added 0.317 g. of 10% palladium-on-carbon and sodium bicarbonate (0.063 g.). The mixture is hydrogenated at 40 p.s.i. for two hours. The catalyst is filtered off, the pH of the filtrate adjusted to 7.3 and most of the dioxane and methanol removed under reduced pressure at a temperature below room temperature. The resulting aqueous solution is washed twice with methylene chloride and the aqueous phase is freeze dried. The freeze dried material is stirred with anhydrous methanol (20 ml.) and the insoluble inorganic material filtered off. The filtrate is evaporated below room temperature to afford 0.208 g. of sodium 6β-phenylacetamido-6-methoxypenicillanate.

IR: 5.65μ (β-lactam), 5.95μ (amide I) and 6.19μ (COO—);

NMR: 2.58 tau (s), ($C_6H_5$); 4.45 tau (s), (5H); 5.72 tau (s), (3H); 6.27 tau (s), ($COCH_2C_6H_5$); 6.48 tau (s), ($OCH_3$); and 8.55 tau (s) and 8.58 tau (s), (gem $CH_3$).

EXAMPLE 4

6β-Phenoxyacetamido-6-methoxypenicillanic Acid Sodium Salt

Step A: Benzyl 6β-phenoxyacetamido-6-methoxypenicillanate

To a solution of benzyl 6β-azido-6-methoxypenicillanate (0.075 g.) in dioxane (4.0 ml.) containing phenoxyacetic anhydride (0.403 g.) is added platinum oxide (0.075 g.) and the mixture is hydrogenated for 18 hours with agitation under 34 p.s.i. of hydrogen. The resulting mixture is concentrated in vacuo at room temperature, and the residue is absorbed on a column containing 20 g. of silica gel with benzene. The product is eluted from the absorbate with chloroform along with phenoxyacetic acid. The combined fractions consisting of 0.377 g. are dissolved in chloroform and washed three times with a 5% solution of sodium bicarbonate. The chloroform solution is then concentrated, and the residue is rechromatographed on 5 g. of silica gel which is eluted with 2–3% ethyl acetate/methylene chloride, and the eluate is evaporated to afford benzyl 6β-phenoxyacetamido-6-methoxypenicillanate.

IR: 3.00μ, 5.63μ, 5.74μ, 5.91μ

Step B: 6β-Phenoxyacetamido-6-methoxypenicillanic Acid Sodium Salt

A solution of benzyl 6β-phenoxyacetamido-6-methoxypenicillanate (0.028 g.) in 8 ml. of solvent (dioxane: methanol:water - 1:2:1) containing 0.028 g. of 10% platinum-on-charcoal is hydrogenated at 40 p.s.i. for one hour. The catalyst is removed by filtration, and the organic solvents are removed by evaporation in vacuo at room temperature to afford 6-methoxy phenoxypenicillanic acid to which is added a solution of sodium bicarbonate (0.06 g.) in water (10.0 ml.). The resulting agueous solution is then extracted with a small quantity of methylene chloride and lyophilized to afford sodium 6β-phenoxyacetamido-6-methoxypenicillanate.

IR: 5.66μ, 5.91μ, 6.0μ

EXAMPLE 5

Sodium 6β-methoxy-6-phenylacetamidopenicillanate

Step A: Benzyl 6β-bromo-6-methoxypenicillanate

To a solution of benzyl 6-diazopenicillanate (2.0 g.) in methylene chloride (20 ml.) is added a cold solution of N-bromoacetamide (56 g.) in methanol (20 ml.). The mixture is kept at ambient temperature for 30 minutes and then the solvents rapidly removed under reduced pressure. The gummy residue is dissolved in methylene chloride and washed with an aqueous sodium bicarbonate solution. The methylene chloride solution is dried over magnesium sulfate, filtered and evaporated. The residue is chromatographed on a column of silica gel (60 g.) which is eluted with a 1:1 mixture of a hexane and methylene chloride solution. A center fraction of 860 mg. of benzyl 6β-bromo-6-methoxypenicillanate is obtained which solidifies on standing. A sample, recrystallized from ether-petroleum ether melts at 90°–91° C. NMR is $CDCl_3$ 4.55 tau (s), (5H); 5.48 tau (s), (3H); 6.36 tau (s), ($OCH_3$); 8.4 tau (s), 8.62 tau (s), (gem $CH_3$). IR is 5.62μ (β-lactam) and 5.78β (ester) (nujol mull).

Elemental analysis Calc: C, 48.01; H, 4.53; N, 3.50; Br, 19.96; Found: C, 47.53; H, 4.30; N, 3.60; Br, 20.65.

Step B: Benzyl 6-α-azido-6-methoxypenicillanate

A solution of benzyl 6β-bromo-6-methoxypenicillanate (640 mg.) and 435 mg. of lithium azide in 5 ml. of dimethylformamide is kept at 30°–35° C. for 6 hours. The dimethylformamide is evaporated under high vacuum and the residue taken up in a mixture of 50 ml. of carbon tetrachloride and 75 ml. of water. The aqueous layer is descarded, and the organic layer is washed twice more with water to remove residual dimethylformamide. The carbon tetrachloride phase is dried and evaporated and the residual oil chromatographed on a column of 20 g. silica gel. Elution with 50% hexane-methylene chloride gives 0.56 g. of benzyl 6-α-azido-6-methoxypenicillanate. NMR in CDCl$_3$ is 4.73 tau (s), (5H); 5.5 tau (s), (3H); 6.43 tau (s), (OCH$_3$); 8.41 tau (s) and 8.62 tau (s), (gem CH$_3$). IR is 4.74μ (azide), 5.60μ (β-lactam) and 5.76μ (ester) (film).

Elemental analysis for C Calc.: C, 53.03; H, 5.0, N, 15.46; Found: C, 52.92; H, 5.13; N, 15.69.

Step C: Benzyl 6β-methoxy-6-phenylacetamidopenicillanate

A mixture of benzyl 6-α-azido-6-methoxypenicillanate (150 mg.), diisopropyl ethylamine (0.1 ml.) and 75 mg. of 10% palladium-on-charcoal catalyst in dry ethylacetate (1.5 ml.) is hydrogenated at atmospheric pressure and room temperature for 3 hours. To the resulting solution of bexnyl 6-α-amino-6-methoxypenicillanate is added a solution of phenylacetic anhydride (200 mg.) in methylene chloride (5). The mixture is stirred at room temperature for 20 minutes, then the catalyst is removed by filtration and the solvents evaporated. The residue is chromatographed on 20 g. of silica gel. Methylene chloride is passed through the column until the eluate is free of phenylacetic acid, and the product is eluted with 2% ethylacetate in methylene chloride. 75 Mg. of benzyl 6β-methoxy-6-phenylacetamidopenicillanate is obtained.

NMR; 2.63 tau (s) and 2.68 tau (s), (phenyl); 4.3 tau (s), (5H); 4.8 tau (s), (OCH$_2$C$_6$H$_5$); 5.53 tau (s), (3H); 6.35 tau (s);

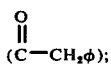

6.51 tau (s), (OCH$_3$); 8.43 tau (s) and 8.61 tau (s), (gem CH$_3$). IR is 5.65μ (β-lactam), 5.75μ (ester) and broad band 5.92–6.02μ (amide) (film).

Step D: Sodium 6β-methoxy-6-phenylacetamidopenicillanate

A solution of 75 mg. of benzyl 6β-methoxy-6-phenylacetamidopenicillanate and 24 mg. of sodium bicarbonate in 2.2 ml. of dioxane, 2.5 ml. water and 1.2 ml. of methanol is hydrogenated in the presence of 75 mg. of 10% palladium-on-charcoal catalyst at room temperature at 30 p.s.i.g. for two hours. The cartalyst is filtered off and the filtrate evaporated under vacuum to dryness. The residue is taken up in water, extracted once with methylene chloride and the aqueous layer freeze-dried. 51 mg. of solid is obtained containing sodium 6β-methoxy-6-phenylacetamidopenicillanate.

IR: 5.67μ (lactam)
NMR: (Solvent - D$_2$O) 2.67 tau (s), (phenyl); 4.53 tau (s), (5H); 5.72 tau (s), (3H); 6.38 tau (s), (φ—CH$_2$); 6.58 tau (s), (OCH$_3$); 8.45 tau (s) and 8.49 tau (s), (gem CH$_3$).

EXAMPLE 6

6-α-Azido-6-bromopenicillanic Acid

Step A: N,O-Bis-trimethylsilyl 6-aminopenicillanate
A suspension of 6-aminopenicillanic acid (0.433 g., 0.002 mole) in chloroform (8 ml.) and hexamethyldisilazane (2 ml.) is heated at reflux for 24 hours protected from moisture. The chloroform and the excess hexamethyldisilazane are removed at reduced pressure leaving an amber-colored, viscous oily residue (665 mg.) of N,O-bis-trimethylsilyl 6-aminopenicillanate The IR and NMR spectra are in agreement with the structure.

Step B: Trimethylsilyl 6-diazopenicillanate
A solution of N,O-bis-trimethylsilyl 6aminopenicillanate (0.53 g.) in chloroform (5 ml.) and trifluoroacetic acid (8 drops) is stirred in an ice bath and isoamyl nitrite (0.3 ml.) added. After one hour, an infrared absorption spectrum is taken and a strong band at 4.78μ (representing the presence of the diazo group) is present. The solution is used directly in the next step.

Step C: 6-α-Azido-6-bromopenicillanic Acid
The chloroform solution of trimethylsilyl 6-diazopenicillanate is diluted with cold nitromethane (8 ml.). Methylene chloride solutions (5 ml.) of triethylammonium azide and 5 ml. bromine azide (both in excess of the required amounts) are added in succession. Nitrogen gas is evolved. After about 5 minutes, 10 ml. of 0.1N sodium thiosulfate solution is added. A few drops of 3N hydrochloric acid are also added to adjust the solution to pH 3, and the layers are separated. The aqueous phase is extracted twice more with chloroform. The combined chloroform extracts are washed once with water, dried, filtered and concentrated leaving 0.104 g. of 6-α-azido-6-bromopenicillanic acid. The infrared absorption spectrum (CHCl$_3$ solution) shows the presence of significant bands at 4.7μ (azido), at 5.6μ (β-lactam structure), and at 5.77μ (carboxylic acid).

EXAMPLE 7

Benzyl 6β-azido-6-methoxypenicillanate

Step A: Epimerization of benzyl 6β-bromo-6-methoxypenicillanate
A solution of benzyl 6β-bromo-6-methoxypenicillanate (200 mg.) and lithium bromide (0.2 g.) in dimethylformamide (1.5 ml.) is stirred at room temperature overnight. The DMF is removed in vacuo, and the residue is taken up in chloroform and washed with water. The chloroform solution is evaporated leaving an equilibrium mixture containing 23% of the β-bromo isomer and 77% of the α-bromo isomer as determined by NMR analysis. Chromatography on silica gel with gradient elution by increasing concentration of methylene chloride in hexane yields 90 mg. of crystalline benzyl 6-α-bromo-6-methoxypenicillanate, m.p. 41°–43° C. NMR is 4.26 tau (s), (5H); 5.48 tau (s), (3H); 6.38 tau (s), (OCH$_3$); 8.47 tau (s) and 8.60 tau (s), (gem CH$_3$). IR is 5.59μ (β-lactam) and 5.75μ (ester) (nujol mull).

Step B: Benzyl 6β-azido-6-methoxypenicillanate
A solution of 90 mg. of benzyl 6-α-bromo-6-methoxypenicillanate (m.p. 41°–43° C.) in 1.5 ml. of N lithium azide in dimethylformamide is kept at room temperature for 3 hours. The dimethylformamide is pumped off in vacuo and the residue taken up in carbon tetrachloride and water. The mixture is centrifuged and the upper aqueous layer removed. The organic layer is washed three times with water, then dried and evaporated, giving 50 mg. of the benzyl ester 6β-azido-6-methoxypenicillin identical with the compound obtained in Example 1, Step C.

EXAMPLE 8

6β-(D-α-aminophenylacetamido)-6-methoxypenicillanic Acid

Step A: D(—)-α-azidophenylacetyl Chloride

D(−)-α-azidophenylacetic acid (2.29 g.) is dissolved in benzene and the solution cooled to 10° C. in an ice bath. Thionyl chloride (11.5ml.) is added dropwise. The reaction mixture is warmed to room temperature and then refluxed for ½ hour. The reaction mixture is cooled to room temperature and the solvent is evaporated on the vacuum pump to afford 2.5 g. of D(−)-α-azidophenylacetyl chloride as a yellow oil.

IR: $\lambda_{max.}{}^{cm+1}$ (CH$_2$Cl$_2$) 2120 (azido), 1790 (C=O).

Step B: 6β-(D-α-aminophenylacetamido)-6-methoxypenicillanic Acid

Benzyl 6β-azido-6-methoxypenicillanate (1.0 g.) is dissolved in dry ethyl acetate (80 ml.), N,N-diisopropylethylamine (4 ml.) and 10% palladium on carbon (1.0 g.) is added. The reaction mixture is stirred overnight under hydrogen at atmospheric pressure. The catalyst is filtered off and the solvent evaporated. The residue is dissolved in methylene chloride (100 ml.) and placed in an ice bath at 10° C. Pyridine (20 ml.) is added and then D(−)-α-azidophenylacetyl chloride (1.45 g.) added in one portion. After stirring 45 minutes the mixture is poured onto ice containing sodium bicarbonate (1.0 g.). The two layers are separated and the aqueous layer washed successively with 3 portions of methylene chloride. The combined methylene chloride layers are washed with water, dried over magnesium sulfate, filtered and evaporated to afford a dark red oil. This reaction is repeated two more times and the products combined and placed on a column of silica gel (60 gm.) in benzene. Elution is with benzene with 200 ml. fractions being taken. Fractions 11–23 contain 0.981 g. of product which is dissolved in methanol (100 ml.) and water (100 ml.) added 1.96 gm. of 10% palladium on carbon is added and the mixture placed on a Parr Shaker for two hours. The catalyst is removed by filtration. The organic solvents are removed by distillation. The remaining aqueous solution is washed with two portions of methylene chloride, the combined methylene chloride solutions are washed once with water. The combined aqueous layers are freeze dried to afford 0.5 gm. of 6β-(D-α-aminophenylacetamide)-6-methoxypenicillanic acid. TLC: $R_f$ 0.65 in butanol, acetic acid and water (3:1:1) IR: $\lambda_{max.}{}^{cm-1}$ nujol 1765 (β-lactam), 1700 (amide), 1600 (COO −) NMR: (CD$_3$OD) 7.4 (m, phenyl), 5.55 (s, 6H), 4.1 (s, 3H), 3.5 (s, —OCH$_3$), 1.39 and 1.12, (s, 2 CH$_3$'s).

EXAMPLE 9

Sodium 6-methoxy-6-phenylacetamidopenicillanate

Benzyl 6-bromo-6-phenylacetamidopenicillanate (1.06 g.) is treated with 0.28 ml. of triethylamine in 10 ml. of methylene chloride to form benzyl 6-phenylacetiminopenicillanate which is reacted with methanol to afford benzyl 6-methoxy-6-phenylacetamidopenicillanate. The ester is hydrogenated with palladium on charcoal catalyst in aqueous methanol in the presence of one equivalent of sodium bicarbonate to afford sodium 6-methoxy-6-phenylacetamidopenicillanate.

EXAMPLE 10

Sodium 6-Thienylacetamido-6-methylthiopenicillanate

Step A: Benzyl 6-bromo-6-methylthio penicillanate

The millimoles of benzyl diazo penicillanate dissolved in methylene chloride (100 ml.) is cooled to −40° C. under N$_2$. To this, 12 millimoles of methylsulfenyl bromide in methylene chloride (100 ml.) is added dropwise with vigorous stirring. Nitrogen evolution is immediate. After addition of the reagent (15 minutes) at −40° C. the mixture is allowed to warm gradually to −5° C. Saturated sodium bicarbonate solution is added and the organic layer separated and washed with water. After drying over sodium sulfate the solvent is removed at room temperature in vacuo to afford benzyl 6-bromo-6-methylthio penicillanate. The crude product is evaluated by ir (loss of diazo 2100 cm$^{-1}$, presence of β-lactam 1790 cm$^{-1}$) and positive Beilstein test for halogen. The crude product may be further purified by preparative tlc or column chromatography.

Step B: Preparation of Benzyl 6-azido-6-metylthio penicillanate

Ten millimoles of benzyl 6-bromo-6-methylthio penicillanate are heated for 4 minutes at 68° C. in 60 ml. DMF which contains 10 millimoles lithium azide. The solution is diluted with 300 ml. water and extracted 2 × 50 ml. chloroform. The chloroform layer is washed 3 × 100 ml. water and dried over anhydrous sodium sulfate. The solution is filtered and the solvent removed to afford preparation of benzyl 6-azido-6-methylthio penicillanate.

Step C: Preparation of benzyl 6-thienylacetamido-6-methylthio penicillanate

Ten millimoles of benzyl 6-azido-6-methylthio penicillanate are dissolved in 50 ml. of ethyl acetate and 10 millimoles of thienylacetic anhydride, 0.1 ml. pyridine and 800 mg. 10% palladium on carbon are added. The mixture is hydrogenated at room temperature for one hour. The catalyst is removed by filtration and the residue evaporated to afford benzyl 6-thienylacetamido-6-methylthio penicillanate.

Step D: Sodium 6-thienylacetamido-6-methylthio penicillanate

By following the procedure of Example 1, Step E, and by substituting benzyl 6-thienylacetamido-6-methylthio penicillanate for the benzyl 6β-acetamido-6-methoxy penicillanate described therein, there is obtained sodium 6-thienylacetamido-6-metylthio penicillanate.

Step E: Sodium 6-thienylacetamido-6-ethylthio penicillanate

By following the procedure of Step A, except that ethyl sulfenylbromide is used as reagent, the intermediate compound benzyl -6-bromo-6-ethylthio penicillanate is prepared. This is used, following the Steps B-D to prepare sodium 6-thienylacetamido-6-ethylthio penicillanate.

EXAMPLE 11

6-Methoxy-6-Phenylmalonacetamidopenicillanic Acid and Disodium Salt

Step A: Benzyl Phenylmalonic acid

An ether solution of phenyldiazomethane is prepared by adding 87 g. (0.31 mole) of N-nitroso-N-benzyl-p-toluenesulfonamide portionwise over one hour to a well stirred mixture of 17 g. of sodium methoxide (0.315 mole) in 60 ml. of methanol and 360 ml. of ether. The thick pink slurry is refluxed for 20 minutes, than cooled and 300 ml. of ice water is added. The organic phase is washed with 3 × 200 ml. of water, dried over sodium sulfate and filtered to yield 360 ml. of a dark red etheral solution of phenyldiazomethane. To a solution of phenylmalonic acid (18.2 g) in 200 ml. of ether is added 350 ml. of the phenyldiazomethane ether solution over ten minutes, while maintaining the temperature at 0°–5° C (nitrogen evolution). The yellow solution is stirred for ten minutes, 500 ml. of water is added and the pH of the mixture adjusted to pH=10 with 2N potassium hydroxide. The layers are separated, the water layer is extracted with 500 ml. of ethyl acetate, and the combined organic phases extracted with 250 ml. of water. Ethyl acetate, 500 ml., is added to the combined aqueous extracts and adjusted to pH=2 with 2N hydrochloric acid with stirring and ice cooling. The aqueous phase is extracted with 200 ml. of ethyl acetate, the combined organic phases are dried over sodium sulfate and concentrated to dryness to yield 25 g. of yellow oil. A TLC (silica gel/10%MeOH in $CH_2Cl_2$) showed two spots, Rf 0.1 and Rf 0.5. Chromatography on 250 g. of silica gel elution with 2% methanol in methylene chloride yielded 14 g. (52%) of pure benzyl phenylmalonic acid, m.p. 45°–50° C, single spot by TLC, Rf 0.5. The IR in morpholine is consistent with the assigned structure, an ester band at 58$\mu$ and a broad carboxylate band at 6.3$\mu$.

Step B: Benzyl Phenylmalonic Acid Chloride

Eight grams of benzyl phenylmalonic acid is dissolved in 8 ml. of oxalyl chloride and let stand at room temperature for one hour. The excess oxalyl chloride is removed under vacuum (bath temp. 25° C) and the residue flushed with 10 ml. of dry benzene to yield about 8 g. of benzyl phenylmalonic acid chloride as a pale yellow oil, which is used immediately in the next step. An N M R in $CDCl_3$ showed a shift in the $\phi CH$ proton from 4.8$\tau$ to 5.0$\tau$. The IR is consistent with the assigned structure with an acid chloride band at 5.6$\mu$ and a benzyl ester band at 5.7$\mu$.

Step C: Benzyl 6-Amino-6-methoxypenicillinate

Eight grams of benzyl 6-azido-6-methoxypenicillinate, dissolved in a mixture of 200 ml. of ethyl acetate and 12 ml. of N,N-diisopropylethylamine is hydrogenated over 16 g. of 10% palladium-on-carbon catalyst at room temperature and 40 psi. for 50 minutes. The catalyst is filtered off and the filtrate concentrated under vacuum at room temperature and pumped to yield 8.0 g. of a tan oil. The IR (in dichloromethane) showed a strong lactam band at 5.6$\mu$, an ester band of equal intensity at 5.85$\mu$, while the azide band of the starting material is totally absent. A TLC (silica gel/2% MeOH in $CH_2Cl_2$) showed several spots with the desired amine, Rf. 0.54, giving a pink color with ninhydrin spray. The oil is used without further purification in the next step.

Step D: Dibenzyl 6-Methoxy-6-phenyl-malonacetamidopenicillinate

Eight grams of benzyl 6-amino-6-methoxypenicillinate is dissolved in 160 ml. of dichloromethane and chilled to −5° C. Pyridine (4.0 g) is added followed by the dropwise addition of 8 g. of benzyl phenylmalonic acid chloride in 160 ml. of dichloromethane over a 5 minute period. The pH of the pale yellow solution is neutral. After stirring for 30 minutes at room temperature, the mixture is washed with 3 × 200 ml. of water, the organic layer is dried over sodium sulfate and concentrated to dryness to yield 15 g. of a yellow oil. A TLC (silica gel/2% MeOH in $CH_2Cl_2$) shows several spots with major components at Rf's 0.5, 0.6, and 0.7, with the desired amide at Rf 0.6 prevailing. Chromatography on 300 g. of silica gel (Baker), eluted with 200 ml. portions of dichloromethane with fractions 11–24 containing 4.0 g. of purified product, showing the major spot at Rf 0.6 and some minor impurities. A second similar chromatography on 100 g. of silica gel gave 2.0 g (15% over two steps) of pure dibenzyl 6-methoxy-6-phenylmalonacetamidopenicillinate, single spot, Rf 0.6. The IR is consistent with the assigned structure, with a lactam band at 5.65$\mu$, an ester band of equal intensity at 5.75$\mu$ and an amide band of lesser intensity at 5.9$\mu$.

Step E: 6-Methoxy-6-phenylmalonacetamidopenicillanic Acid Disodium Salt

A solution of 2.0 g. of dibenzyl 6-methoxy-6-phenylmalonacetamidopenicillinate in 200 ml. of a mixture of dioxane, methanol and water (1:2:1) is hydrogenated over 4 g. of 10% palladium-on-carbon at room temperature, at 40 psi. for one hour. After filtration and concentration to dryness at room temperature, the 6-methoxy-6-phenylmalonacetamido penicillanic acid is converted to its disodium salt by dissolving in 25 ml. of water containing 0.5 g. of sodium bicarbonate. The aqueous solution is extracted with 3 × 25 ml. of dichloromethane, then freeze-dried to yield 1.2 g. of pure 6-methoxy-6-phenylmalonacetamidopenicillanic acid disodium salt (74%) as a pale yellow powder. The IR is consistent with the proposed structure, with $\alpha$ $\beta$-lactam band at 5.65$\mu$, an amide band at 5.95$\mu$ and a broad carboxylate band at 6.3$\mu$. A TLC (silica gel/n-BuOH-$H_2O$-HOAc, 4:1:1) shows essentially a single spot. A Karl Fisher titration gave 2.5% $H_2O$ (after correction due to $NaHCO_3 \rightarrow H_2O + CO_2 + Na_2CO_3$). Estimating 4% of sodium bicarbonate and 2% of water to be present, gives the corrected elemental analysis: Calcd. (corr): C, 45.58; H, 4.02; N, 5.82; S, 6.65; Na, 10.65 Found: C, 45.56; H, 4.24; N, 5.59; S, 6.60; Na, 11.10.

EXAMPLE 12

Benzyl 6-Diazopenicillanate-S-oxide

Step A: Benzyl 6-Aminopenicillanate-S-oxide, p-toluenesulfonic Acid Salt

Benzyl 6-aminopenicillanate p-toluene sulfonic acid salt (.5 g.) is taken up in 25 ml. of methylene chloride, 10 ml. of water and 0.081 g. of sodium bicarbonate is added. The mixture is shaken and the aqueous phase is discarded. The organic phase is dried over $MgSO_4$ and evaporated to give 0.320 g. of benzyl 6-aminopenicillanate which is dissolved in 10 ml. methylene chloride and treated with 0.180 g. of m-chloro per benzoic acid for 1 hour. The mixture is diluted with methylene chloride and washed three times with 5% $NaHCO_3$, and once with water. The methylene chloride solution is dried, filtered and evaporated. The residue is taken up in acetone (10 ml.) cooled to −5° C. and 0.200 g. of p-toluene sulfonic acid is added. The mixture is allowed to stand at −5° C. for 1 hour. The crystallized solid is filtered and washed with acetone at 0° C. to give benzyl 6-aminopenicillanate-S-oxide, p-toluenesulfonic acid salt. m.p. 159°–161° C.

I.R.: 5.57 ($\beta$ lactam carbonyl), 5.72 $\mu$ (ester carbonyl)

Step B: Benzyl 6-aminopenicillanate-S-oxide

Benzyl 6-aminopenicillanate-1-oxide, p-toluenesulfonic acid salt (0.164 g.) is taken up in 10 ml. of methylene chloride and 10 ml. of water. Sodium bicarbonate (0.028 g.) is added and the mixture is shaken and the organic phase is separated, dried over $MgSO_4$ and evaporated to give 0.102 g. of benzyl 6-aminopenicillanate-S-oxide.

I.R.: 6.62 $\mu$($\beta$ lactam), 5.72 $\mu$ (ester carbonyl).

NMR: 2.61 $\delta$, $\phi$; 4,75 $\delta$ (AB quartet), $CH_2$—$C_6H_5$;

5.07 δ 5.3 δ (5H 6H pair of doublets)
5.34 δ, (3H); 7.75 δ (NH₂); 8.35 8.91, (gem dimethyl).

Step C: Benzyl 6-Diazopenicillanate-S-oxide

Benzyl 6-aminopenicillanate-1-oxide (0.32 g.) is dissolved in 25 ml. of methylene chloride, 10 g. of ice is added and 0.100 g of sodium nitrite. The mixture is shaken and then 0.400 of p-toluene sulfonic acid is added in 4 equal amounts over a period of 10 minutes with vigorous shaking. The aqueous phase is then separated and the yellow organic phase is worked once with water dried over sodium sulfate, and evaporated to afford benzyl 6-diazopenicillanate-S-oxide.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly. Suitable carriers which may be used in the composition include, for example, mannitol, sucrose, glucose or sterile liquids such as water, saline, glycols and oils of petroleum, animal, vegetable or synthetic origin as, for example, peanut oil, mineral oil or sesame oil. Also, in addition to a carrier the instant compositions may include other ingredients such as stabilizers, binders, antioxidants, preservatives, lubricators, suspending agents, viscosity agents or flavoring agents. In addition, there may also be included in the composition other active ingredients to provide a broader spectrum of antibiotic activity.

The dosage to be administered depends to a large extent upon the condition of the subject being treated and the weight of the host, the parenteral route being preferred for generalized infections and the oral route for intestinal infections. In general, a daily dosage consists of from about 15 to about 600 mg. of active ingredient per kg. of body weight of the subject in one or more applications per day.

One typical unit dosage form consists in mixing 120 mg. of the sodium salt of 6-methoxy-6-phenoxyacetamido penicillanic acid with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following example is illustrative Dry-Filled Capsule Containing 120 mg. of the Sodium Salt of 6-methoxy-6-phenoxyacetamidopenicillanic Acid:

|  | Per Capsule |
|---|---|
| Sodium salt of 6-methoxy-6-phenoxyacetamidopenicillanic Acid | 120 mg. |
| Lactose | 20 mg. |
| Magnesium Stearate | 5 mg. |
| Capsule Size No. 3 | 145 mg. |

The sodium salt of 6-methoxy-6-phenoxyacetamidopenicillanic acid is reduced to a No. 60 powder and then lactose and magnesium stearate are passed through a No. 60 bolting cloth onto the powder and the combined ingredients admixed for 10 minutes and then filled into No. 3 dry gelatin capsules.

What is claimed is:
1. The compound of the formula

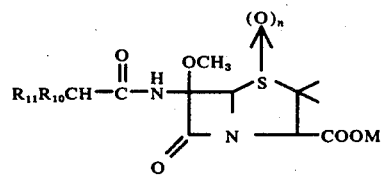

wherein
$R_{10}$ is hydrogen, amino, hydroxy, or carboxy;
$R_{11}$ is hydrogen, phenyl, phenoxy, phenylthio, thienyl, furyl, isothiazolyl, pyridyl, pyridylthio, or phenyl substituted with loweralkyl or loweralkoxy;
$n$ is 0 or 1;
and
M is hydrogen, sodium, potassium, ammonium, lower-alkyl, haloloweralkyl, allyl, loweralkynyl, benzyl, p-methoxybenzyl, o-nitrobenzyl, or phenacyl.
2. The compound of claim 1 wherein $R_{10}$ is hydrogen, carboxy or hydroxy; and $R_{11}$ is phenyl, thienyl, furyl, hydrogen or phenoxy;
3. The compound of claim 1 wherein $R_{10}$ is hydrogen, and M is benzyl.
4. The compound of claim 1 wherein $R_{10}$ is hydrogen, $R_{11}$ is phenyl and M is hydrogen.
5. The compound of claim 1 wherein $R_{10}$ is hydrogen, $R_{11}$ is phenoxy, and M is hydrogen.
6. The compound of claim 1 wherein $R_{10}$ is carboxy, $R_{11}$ is phenyl, and M is hydrogen.

* * * * *